US010869933B2

(12) United States Patent
Gu et al.

(10) Patent No.: US 10,869,933 B2
(45) Date of Patent: Dec. 22, 2020

(54) OLIGOMER-PHENOTHIAZINE CONJUGATES

(71) Applicant: Nektar Therapeutics, San Francisco, CA (US)

(72) Inventors: Xuyuan Gu, Foster City, CA (US); Jennifer Riggs-Sauthier, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 16/599,605

(22) Filed: Oct. 11, 2019

(65) Prior Publication Data

US 2020/0038517 A1 Feb. 6, 2020

Related U.S. Application Data

(60) Division of application No. 15/968,561, filed on May 1, 2018, now Pat. No. 10,485,877, which is a continuation of application No. 13/146,612, filed as application No. PCT/US2010/022342 on Jan. 28, 2010, now abandoned.

(60) Provisional application No. 61/148,016, filed on Jan. 28, 2009.

(51) Int. Cl.
*A61K 47/60* (2017.01)

(52) U.S. Cl.
CPC .................................... *A61K 47/60* (2017.08)

(58) Field of Classification Search
CPC ...................................................... A61K 47/60
See application file for complete search history.

(56) References Cited

U.S. PATENT DOCUMENTS

| 2,519,886 | A | 8/1950 | Charpentier |
| 2,530,451 | A | 11/1950 | Charpentier |
| 2,607,773 | A | 8/1952 | Berg et al. |
| 3,987,042 | A | 10/1976 | Gueremy et al. |
| 4,985,419 | A | 1/1991 | Garret et al. |
| 5,672,662 | A | 9/1997 | Harris et al. |
| 6,992,082 | B2 | 1/2006 | Finer et al. |
| 7,122,201 | B2 | 10/2006 | Yu et al. |
| 2005/0080075 | A1* | 4/2005 | Nichols .................. A61K 47/61 514/225.5 |
| 2005/0136031 | A1 | 6/2005 | Bentley et al. |
| 2012/0046279 | A1 | 2/2012 | Gu et al. |
| 2018/0243429 | A1 | 8/2018 | Gu et al. |

FOREIGN PATENT DOCUMENTS

| GB | 641452 | 8/1950 |
| WO | WO 02/098949 | 12/2002 |
| WO | WO 2005/058367 | 6/2005 |
| WO | WO 2008/112257 | 9/2008 |

OTHER PUBLICATIONS

Schafer et al. Drug Discovery Today, 2008, 13 (21/22), 913-916.*
Horig et al. Journal of Translational Medicine 2004, 2(44), 1-8.*
Ban, et al., "Electrical Communication between Glucose Oxidase and Electrodes Mediated by Phenothiazine-Labeled Poly(ethylene oxide) Bonded to Lysine Residues on the Enzyme Surface," Anal. Chem., vol. 75, pp. 910-917, (2003).
Chen, et al., "Synthesis and Properties of ABA Amphiphiles," J. Org. Chem., vol. 64, pp. 6870-6873, (1999).
Cho, et al., "Intramolecular Exciplex and Intermolecular Excimer Formation of 1,8-Naphthalimide-Linker-Phenothiazine Dyads," J. Phys. Chem. B., vol. 110, pp. 4576-4582 (2006).
Ertl, et al., "Fast Calculation of Molecular Polar Surface Area as a Sum of Fragment-Based Contributions and Its Application to the Prediction of Drug Transport Properties," J. Med. Chem., vol. 43, pp. 3714-3717, (2000).
Kelder, et al., "Polar Molecular Surface as a Dominating Determinant for Oral Absorption and Brain Penetration of Drugs," Pharmaceutical Research, vol. 16, No. 10, pp. 1514-1519, (1999).
O'Neil, et al., "Dixyrazine," The Merck Index. An Encyclopedia of Chemicals, Drugs, and Biologicals, monograph 3385, pp. 572, (2006).
PCT International Search Report corresponding to PCT Application No. PCT/US2010/022342 dated May 28, 2010.
PCT International Preliminary Report on Patentability corresponding to PCT Application No. PCT/US2010/022342 dated Aug. 1, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).

(Continued)

*Primary Examiner* — Yong L Chu
(74) *Attorney, Agent, or Firm* — Jacqueline F. Mahoney

(57) ABSTRACT

The invention relates to (among other things) oligomer-phenothiazine conjugates and related compounds. A conjugate of the invention, when administered by any of a number of administration routes, exhibits advantages over un-conjugated phenothiazine compounds.

18 Claims, No Drawings

(56) References Cited

OTHER PUBLICATIONS

Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Notification of the First Office Action corresponding to Chinese Application No. 201080005673.6 dated Sep. 19, 2012.
Notification of the Second Office Action corresponding to Chinese Application No. 201080005673.6 dated Jul. 12, 2013.
Examination Report corresponding to European Application No. 10 703 204.7-1216 dated Oct. 4, 2012.
Notice of Reasons for Rejection corresponding to Japanese Patent Application No. 2011-548281 dated May 26, 2014.
First Office Action corresponding to Mexican Application No. MX/a/2011/007940 dated Jun. 5, 2013.
Second Office Action corresponding to Mexican Application No. MX/a/2011/007940 dated Nov. 22, 2013.
Australian Examination Report corresponding to Australian Patent Application No. 2010208274 dated Sep. 12, 2014.
Canadian Office Communication corresponding to Canadian Patent Application No. 2,749,126 dated Sep. 2, 2015.
Canadian Office Communication corresponding to Canadian Patent Application No. 2,749,126 dated Apr. 26, 2016.
European Office Communication corresponding to European Patent Application No. 10 703 204.7-1453 dated Jun. 22, 2016.
European Office Communication corresponding to European Patent Application No. 10 703 204.7-1453 dated Feb. 22, 2017.
Indian Examination Report corresponding to Indian Patent Application No. 5375/CHENP/2011 dated Oct. 17, 2017.
Third Office Action corresponding to Mexican Application No. MX/a/2011/007940 dated Jun. 24, 2014.
Fourth Office Action corresponding to Mexican Application No. MX/a/2011/007940 dated Jun. 24, 2014.

\* cited by examiner

OLIGOMER-PHENOTHIAZINE CONJUGATES

CROSS REFERENCE TO RELATED APPLICATION

This application is a divisional application of U.S. patent application Ser. No. 15/968,561, filed May 1, 2018, now U.S. Pat. No. 10,485,877, which is a continuation application of U.S. patent application Ser. No. 13/146,612, filed Nov. 3, 2011, now abandoned, which is a 35 U.S.C. § 371 application of International Application No. PCT/US2010/022342, filed Jan. 28, 2010, designating the United States, which claims the benefit of priority under 35 U.S.C. § 119(e) to U.S. Provisional Patent Application Ser. No. 61/148,016, filed Jan. 28, 2009, the disclosures of which are incorporated herein by reference in their entireties.

FIELD OF THE INVENTION

This invention comprises (among other things) chemically modified phenothiazines that possess certain advantages over phenothiazines lacking the chemical modification. The chemically modified phenothiazines described herein relate to and/or have application(s) in (among others) the fields of drug discovery, pharmacotherapy, physiology, organic chemistry and polymer chemistry.

BACKGROUND OF THE INVENTION

Phenothiazines have been shown to possess antihistaminic, sedative, anti-motion-sickness, antiemetic, and anticholinergic effects. They are generally indicated for: 1) amelioration of allergic reactions to blood or plasma; 2) in anaphylaxis as an adjunct to epinephrine and other standard measures after the acute symptoms have been controlled; 3) for other uncomplicated allergic conditions of the immediate type when oral therapy is impossible or contraindicated; 4) active treatment of motion sickness; 5) preoperative, postoperative, and obstetric (during labor) sedation; 6) prevention and control of nausea and vomiting associated with certain types of anesthesia and surgery; 7) as an adjunct to analgesics for the control of postoperative pain; 8) for sedation and relief of apprehension and to produce light sleep from which the patient can be easily aroused; and 9) intravenously in special surgical situations, such as repeated bronchoscopy, ophthalmic surgery, and poor-risk patients, with reduced amounts of meperidine or other narcotic analgesic as an adjunct to anesthesia and analgesia. Phenothiazines are also indicated as tranquilizers in veterinary medicine. Recently, phenothiazines have been shown to be inhibitors of KSP kinesin which is involved in microtubule-mediated mitotic spindle-related distribution of replicate copies of the genome to each daughter cell that result from cell division. Therefore, phenothiazines may have a role in cancer treatment as well. However, with the use of phenothiazines some incidents of venous thrombosis at the injection site have been encountered. Other clinical case reports involving the use of promethazine HCl have indicated irritation and other serious adverse reactions at the local area of injection particularly gangrene at the extremity of the injection site. Promethazine hydrochloride has also been reported to raise plasma creatine kinase levels after intramuscular injection, which is an indication of muscle irritation.

Therefore, pharmacotherapy with phenothiazines would be improved if these and/or other side effects associated with their use could be decreased or if their pharmacology may be improved. Thus, there is a large unmet need for developing novel phenothiazine compounds.

The present invention seeks to address these and other needs in the art.

SUMMARY OF THE INVENTION

In one or more embodiments of the invention, a compound is provided, the compound comprising a phenothiazine residue covalently attached via a stable or degradable linkage to a water-soluble, non-peptidic oligomer.

Exemplary compounds of the invention include those having the following structure:

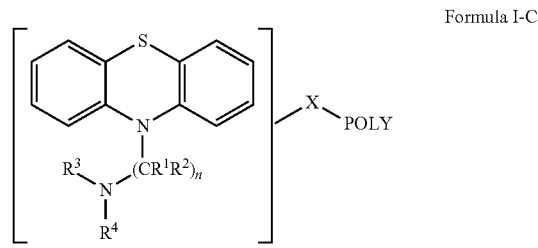

Formula I-C wherein:

$R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle;

n is an integer equal to or greater than one;

X is a spacer moiety; and

POLY is a water-soluble, non-peptidic oligomer.

Further exemplary compounds include those having the following structure:

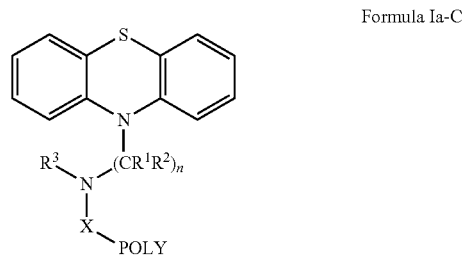

Formula Ia-C wherein:

$R^1$, $R^2$, and $R^3$, each independently are selected from the group consisting of hydrogen, unsubstituted alkyl, and substituted alkyl;

n is an integer equal to or greater than one;

X is a spacer moiety; and

POLY is a water-soluble, non-peptidic oligomer.

Exemplary compounds include those having the following structure:

Formula Ib-C

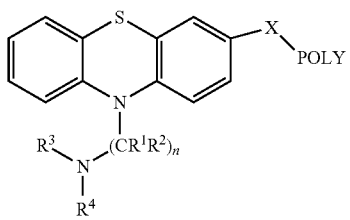

$R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle;
n is an integer equal to or greater than one;
X is a spacer moiety; and
POLY is a water-soluble, non-peptidic oligomer.

The "phenothiazine residue" is a compound having a structure of a phenothiazine compound that is altered by the presence of one or more bonds, which bonds serve to attach (either directly or indirectly) one or more water-soluble, non-peptidic oligomers.

In this regard, any phenothiazine compound having receptor binding activity can be used as a phenothiazine moiety. Exemplary phenothiazine moieties have a structure encompassed by Formula I:

Formula I

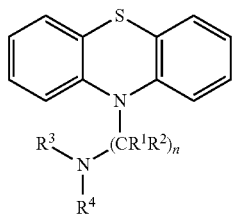

wherein:
$R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle; and
n is an integer equal to or greater than one.

In one or more embodiments of the invention, a composition is provided, the composition comprising a compound comprising a phenothiazine residue covalently attached via a stable or degradable linkage to a water-soluble, non-peptidic oligomer, and optionally, a pharmaceutically acceptable excipient.

In one or more embodiments of the invention, a dosage form is provided, the dosage form comprising a compound comprising a phenothiazine residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a phenothiazine moiety.

In one or more embodiments of the invention, a method is provided, the method comprising administering a compound to a mammal in need thereof, comprising a phenothiazine residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

BRIEF DESCRIPTION OF THE FIGURES

This paragraph is intentionally left blank.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though, the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from about 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidyleathanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of an oligomer, refers to an oligomer having two or more polymers "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as ap-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the therapeutic moiety. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the therapeutic moiety. A composition comprised of bimodal conjugates may, however, include one or more nonconjugate substances such as solvents, reagents, excipients, and so forth.

An "phenothiazine" is broadly used herein to refer to an organic, inorganic, or organometallic compound having a molecular weight of less than about 1000 Daltons and having some degree of activity as a phenothiazine therapeutic. Phenothiazine activity of a compound may be measured by assays known in the art and also as described herein.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it ever reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a conjugate of the invention may provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

Chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding multivalent moiety, arylene). All atoms are understood to have their normal number of valences for bond formation (i.e., 1 for H, 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a phenothiazine residue covalently attached via a stable or degradable linkage to a water-soluble, non-peptidic oligomer.

The "phenothiazine residue" is a compound having a structure of a phenothiazine compound that is altered by the presence of one or more bonds, which bonds serve to attach (either directly or indirectly) one or more water-soluble, non-peptidic oligomers. Exemplary phenothiazines have a structure encompassed by at least one of the structures defined herein as Formula I:

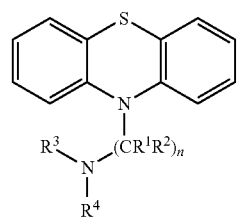

Formula I wherein:
$R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle; and
n is an integer equal to or greater than one.

In one or more embodiments of the invention, a compound is provided, the compound comprising a phenothiazine residue covalently attached via a stable or degradable linkage to a water-soluble, non-peptidic oligomer, wherein the phenothiazine has a structure encompassed by the following formula:

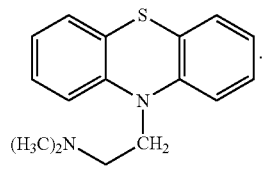

In one or more embodiments of the invention, a compound is provided, the compound comprising a phenothiazine residue covalently attached via a stable or degradable linkage to a water-soluble, non-peptidic oligomer, wherein the phenothiazine has a structure encompassed by the following formula:

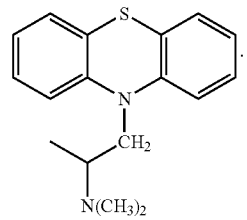 [SMILES: CC(CN1c2ccccc2Sc2ccccc21)N(C)C]

In one or more embodiments of the invention, a compound is provided, the compound comprising a phenothiazine residue covalently attached via a stable or degradable linkage to a water-soluble, non-peptidic oligomer, wherein the phenothiazine is selected from the group consisting of mequitazine, promethazine, promezine, and thiazinamium methylsulfate.

In some instances, phenothiazines can be obtained from commercial sources. In addition, phenothiazines can be obtained through chemical synthesis. Examples of phenothiazines as well as synthetic approaches for preparing phenothiazines are described in the literature and in, for example, U.S. Pat. Nos. 2,519,886, 2,530,451, 2,607,773, 3,987,042, GB Patent No. 641452. Each of these (and other) phenothiazines can be covalently attached (either directly or through one or more atoms) to a water-soluble, non-peptidic oligomer.

Exemplary compounds of the invention include those having the following structure:

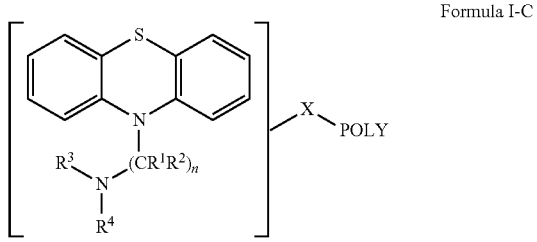

Formula I-C wherein:
$R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle;
n is an integer equal to or greater than one;
X is a spacer moiety; and
POLY is a water-soluble, non-peptidic oligomer.

Further exemplary compounds of the invention include those having the following structure:

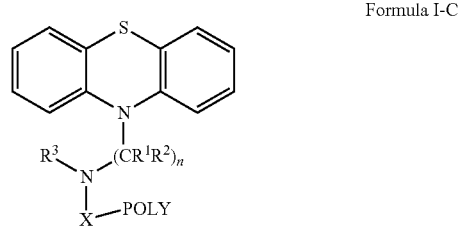

Formula I-C wherein:
$R^1$, $R^2$, and $R^3$, each independently are selected from the group consisting of hydrogen, unsubstituted alkyl, and substituted alkyl;
n is an integer equal to or greater than one;
X is a spacer moiety; and
POLY is a water-soluble, non-peptidic oligomer.

Exemplary compounds of the invention include those having the following structure:

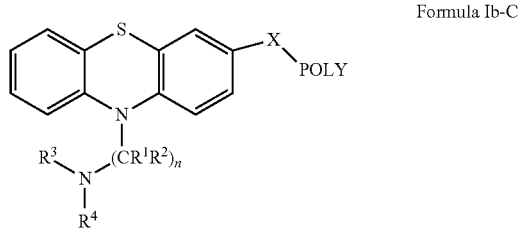

Formula Ib-C $R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle;

n is an integer equal to or greater than one;
X is a spacer moiety; and
POLY is a water-soluble, non-peptidic oligomer.

Use of discrete oligomers (e.g., from a monodisperse or bimodal composition of oligomers, in contrast to relatively impure compositions) to form oligomer-containing compounds may advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate of the invention is at least about 20%.

Assays for determining whether a given compound (regardless of whether the compound includes a water-soluble, non-peptidic oligomer or not) can act as a phenothiazine are known and/or may be prepared by one of ordinary skill in the art and are further described infra.

Each of these (and other) phenothiazine moieties can be covalently attached (either directly or through one or more atoms) to a water-soluble, non-peptidic oligomer.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300 Daltons.

The small molecule drug used in the invention, if chiral, may be obtained from a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The phenothiazine moiety for coupling to a water-soluble, non-peptidic oligomer possesses a free hydroxyl, carboxyl, thio, amino group, or the like (i.e., "handle") suitable for covalent attachment to the oligomer. In addition, the phenothiazine moiety may be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; $\alpha$-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and $\alpha$-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the phenothiazine (in contrast to the step-wise addition of one or more monomers to effectively "grow" the oligomer onto the phenothiazine), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the phenothiazine moiety) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the phenothiazine residue and the water-soluble, non-peptidic oligomer), ), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—, CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— or —RNCO—).

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is formed by reaction of a functional group on a terminus of the oligomer (or nascent oligomer when it is desired to "grow" the oligomer onto the phenothiazine) with a corresponding functional group within the phenothiazine. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazolyl carbonate) on the drug, or vice versa, forms a carbamate linkage. Reaction of an amine on an oligomer with an isocyanate (R—N═C═O) on a drug, or vice versa, forms a urea linkage (R—NH—(C═O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O—(CH_2—CH_2—O)_n—(CH_2)_p—C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group may be capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(═O)O-Q, where Q is preferably selected from N-succinimide, N-sulfosuccinimide, N-phthalimide, N-glutarimide, N-tetrahydrophthalimide, N-norbomene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N═C═O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the phenothiazine may not have a functional group suited for conjugation. In this instance, it is possible to modify (or "functionalize") the "original" phenothiazine so that it does have a functional group suited for conjugation. For example, if the phenothiazine has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule phenothiazine bearing a carboxyl group wherein the carboxyl group-bearing small molecule phenothiazine is coupled to an amino-terminated oligomeric ethylene glycol, to provide a conjugate having an amide group covalently linking the small molecule phenothiazine to the oligomer. This can be performed, for example, by combining the carboxyl group-bearing small molecule phenothiazine with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule phenothiazine bearing a hydroxyl group wherein the hydroxyl group-bearing small molecule phenothiazine is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule phenothiazine moiety bearing a hydroxyl group wherein the hydroxyl group-bearing small molecule phenothiazine moiety is coupled to an oligomeric ethylene glycol bearing an haloformate group [e.g., $CH_3(OCH_2CH_2)_n$ OC(O)-halo, where halo is chloro, bromo, iodo] to result in a carbonate [—O—C(O)—O-] linked small molecule conjugate. This can be performed, for example, by combining a phenothiazine moiety and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule phenothiazine bearing a ketone group by first reducing the ketone group to form the corresponding hydroxyl group. Thereafter, the small molecule phenothiazine now bearing a hydroxyl group can be coupled as described herein.

In still another instance, it is possible to prepare a conjugate of a small molecule phenothiazine bearing an amine group. In one approach, the amine group-bearing small molecule phenothiazine and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule phenothiazine and the carbonyl carbon of the aldehyde-bearing oligomer.

In another approach for preparing a conjugate of a small molecule phenothiazine bearing an amine group, a carboxylic acid-bearing oligomer and the amine group-bearing small molecule phenothiazine are combined, in the presence of a coupling reagent (e.g., DCC). The result is an amide linkage formed between the amine group of the amine group-containing small molecule phenothiazine and the carbonyl of the carboxylic acid-bearing oligomer.

While it is believed that the full scope of the conjugates disclosed herein behave as described, an optimally sized oligomer can be identified as follows.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the phenothiazine or the conjugate of a phenothiazine and a water-soluble non-peptidic polymer has activity as a phenothiazine therapeutic, it is possible to test such a compound. The phenothiazine compounds may be tested using in vitro binding studies to receptors using various cell lines expressing these receptors that have become routine in pharmaceutical industry and described herein.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

$^1$H NMR (nuclear magnetic resonance) data was generated by an NMR spectrometer. A list of certain compounds as well as the source of the compounds is provided below.

Example 1

Synthesis of Small PEG Promethazine Conjugates:

Scheme 1: Synthesis of mPEG$_n$-N-Promethazine conjugates.

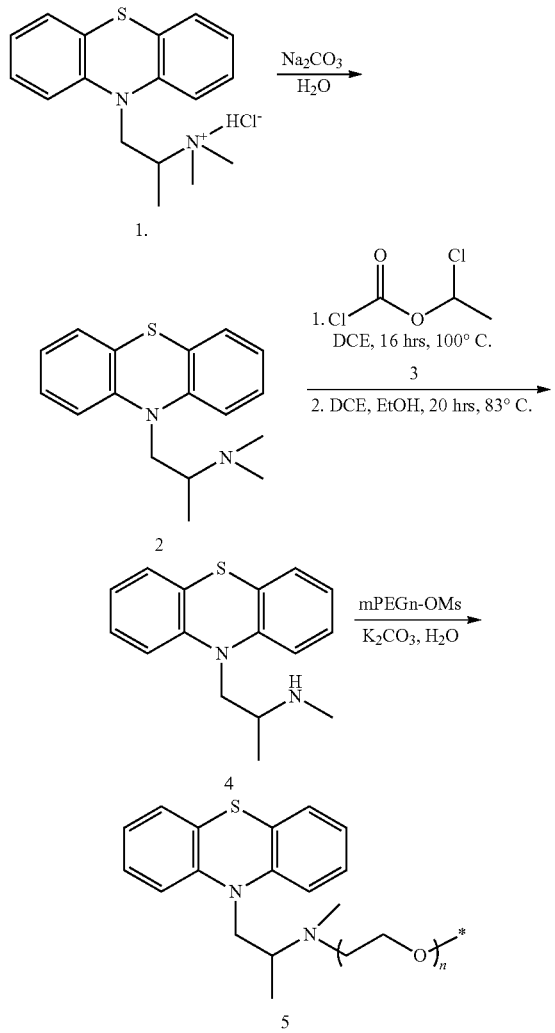

n = 3, 4, 5, 6, 7, 9

Promethazine, 1-chloroethyl chloroformate, dichloroethane (DCE), phosphorous oxychloride (POCl$_3$), sodium borohydride (NaBH$_4$), sodium hydride (NaH), and N,N-dimethylformamide (DMF) were from Sigma-Aldrich (St Louis, Mo.). mPEG$_n$-OMs and mPEG$_n$-Br were from Sai Chemicals (India). Sodium carbonate (Na$_2$CO$_3$), sodium bicarbonate (NaHCO$_3$), sodium sulfate (Na$_2$SO$_4$), potassium carbonate (K$_2$CO$_3$), sodium chloride (NaCl), and sodium hydroxide (NaOH) were from EM Science (Gibbstown, N.J.). DCM was distilled from CaH$_2$.

Desalting of Promethazine.HCl:

The Sigma-Aldrich promethazine.HCl (10 g, 31.2 mmol) was dissolved in H$_2$O (250 mL) in a 500-mL flask. Na$_2$CO$_3$ (8.2 g, 78 mmol) was added in one portion. The salt was first dissolved in water and then a thick oil-like product appeared sticking to the stirring bar. DCM (50 mL) was added to dissolve the product and the solution became clear after 2.5 hrs. The solution was diluted by adding DCM (50 mL) and the organic phase was separated. The aqueous phase was then extracted with DCM (50 mL×2) and the combined organic phases were dried over Na$_2$SO$_4$. After filtration, the solution was concentrated and a viscous product was obtained.

Promethazine

R$_f$=0.26 (DCM:MeOH=10:1), RP-HPLC (betasil C18, 0.5 mL/min, 10-60% ACN in 10 min) 8.45 min, purity >99%, LC-MS (ESI, MH$^+$) 285.3, $^1$H NMR (500 MHz, CDCl$_3$) δ 1.06 (3H, d, J=6.5 Hz), 2.35 (6H, s), 3.05-3.12 (1H, m), 3.69 (1H, dd, J=9, 13.5 Hz), 4.07 (1H, dd, J=4.0, 13.0 Hz), 6.92-6.95 (4H, m), 7.15-7.17 (4H, m).

Demethylation:

The promethazine obtained above (2.71 g, 9.51 mmol) was dissolved in DCE (50 mL) in a 250-mL flask. 1-Chloroethyl chloroformate (12.4 mL, 114 mmol) was added slowly at room temperature. The mixture was heated in oil-bath to 100° C. and the reaction was kept overnight (16 hrs) at this temperature. After cooling down the reaction mixture under the dry N$_2$ atmosphere, the solvent was evaporated under vacuum. The residue was dried under high vacuum for 3 hrs before it was re-dissolved in DCE (25 mL) and ethanol (25 mL). The mixture was heated to 83° C. and reflux was continued at this temperature overnight (20 hrs). After cooling down to the room temperature, the solvents were evaporated and the residue was diluted in DCM (100 mL) and saturated NaHCO$_3$ solution (250 mL). After the organic phase was separated, the aqueous solution was extracted with DCM (50 mL×2) and the combined organic phases were dried over Na$_2$SO$_4$. After filtration and concentration, the resulting residue was loaded onto a Biotage 40M column (1-6% of MeOH in DCM in 16 CV). Only part of the pure product was obtained based on HPLC fraction analysis. The mixture was purified a second time on a Biotage 25M column under the same conditions. The slight yellowish product (1.39 g, 54% yield) was obtained together with a mixture (560 mg, 20%).

N-demethyl-promethazine

R$_f$=0.23 (DCM:MeOH=10:1), RP-HPLC (betasil C18, 0.5 mL/min, 30-60% ACN in 10 min) 3.68 min, LC-MS (ESI, MH$^+$) 271.2. $^1$H NMR (500 MHz, CDCl$_3$) δ 1.16 (3H, d, J=6.5 Hz), 2.38 (3H, s), 3.05-3.12 (1H, m), 3.83 (1H, dd, J=5.0, 13.5 Hz), 3.91 (1H, dd, J=3.0, 13.5 Hz), 6.92-6.96 (4H, m), 7.15-7.19 (4H, m).

General Procedure for N-PEGylation from mPEG$_n$-OMs:

The above secondary amine starting material (about 200 mg, 1 eq) was combined with mPEG$_n$-OMs (1.2 eq) in 12-mL microwave reaction tube. K$_2$CO$_3$ (1.5 eq) and water (1.2 mL) was added. After sealing the tube, the reaction was performed using a 3-stage program (65° C., 2 min, 85° C., 2 min, 100° C., 100 min). After the reaction was complete, the mixture was diluted with NaHCO$_3$ (60 mL) and extracted with DCM (20 mL×3). The combined DCM solution was dried over Na$_2$SO$_4$. After filtration, the solution was concentrated and the resulting residue was purified on a Biotage 25M normal phase column (1-6% MeOH in DCM in 16 CV). The product mixture was purified one more time on under normal phase conditions to collect more pure product. The final fractions were combined and loaded on Biotage reverse phase column (25M, 20% in 5 CV following with 20-65% acetonitrile in water in 20 CV). The product fractions were again combined and acetonitrile was evaporated until the solution become cloudy. The aqueous phase was then extracted with DCM (15 mL×3), with small amount of solid NaCl was added each time in extraction. The combined DCM solution was dried over Na$_2$SO$_4$ and filtrated. The solution was then concentrated and dried under vacuum over 24 hrs before characterization.

General Procedure for N-PEGylation from mPEG$_n$-Br:

The N-PEGylation can be designed using mPEG$_n$-Br using a similar procedure as described above with over 95% conversion. No differences in the work up and purification. The product contained a darker color which was a contaminate from the starting mPEG$_n$-Br and was subsequently removed during the reverse phase purification.

mPEG$_3$-N-promethazine

R$_f$=0.33 (DCM:MeOH=10:1), RP-HPLC (betasil C18, 0.5 mL/min, 30-60% ACN in 10 min) 5.43 min, purity >99%, LC-MS (ESI, MH$^+$) 417.3. $^1$H NMR (500 MHz, CDCl$_3$) δ 1.04 (3H, d, J=6.5 Hz), 2.34 (3H, s), 2.65-2.74 (2H, m), 3.20-3.24 (1H, m), 3.38 (3H, s), 3.51-3.65 (10H, m), 3.70 (1H, dd, J=9.0, 13.0 Hz), 4.03 (1H, dd, J=4.5, 13.5 Hz), 6.91-6.94 (4H, m), 7.14-7.17 (4H, m).

mPEG$_4$-N-promethazine

R$_f$=0.33 (DCM:MeOH=10:1), RP-HPLC (betasil C18, 0.5 mL/min, 30-60% ACN in 10 min) 5.80 min, purity >98%, LC-MS (ESI, MH$^+$) 461.3. $^1$H NMR (500 MHz, CDCl$_3$) δ 1.04 (3H, d, J=6.5 Hz), 2.34 (3H, s), 2.65-2.74 (2H, m), 3.20-3.24 (1H, m), 3.38 (3H, s), 3.51-3.65 (14H, m), 3.70 (1H, dd, J=9.0, 13.5 Hz), 4.03 (1H, dd, J=4.5, 13.0 Hz), 6.91-6.94 (4H, m), 7.14-7.17 (4H, m).

mPEG$_5$-N-promethazine

R$_f$=0.33 (DCM:MeOH=10:1), RP-HPLC (betasil C18, 0.5 mL/min, 30-60% ACN in 10 min) 5.80 min, purity >99%, LC-MS (ESI, MH$^+$) 505.3. $^1$H NMR (500 MHz, CDCl$_3$) δ 1.04 (3H, d, J=6.5 Hz), 2.34 (3H, s), 2.68-2.70 (2H, m), 3.21 (1H, bs), 3.38 (3H, s), 3.52-3.65 (18H, m), 3.70 (1H, dd, J=9.0, 12.5 Hz), 4.02 (1H, dd, J=4.0, 13.0 Hz), 6.91-6.94 (4H, m), 7.15-7.17 (4H, m).

mPEG$_6$-N-promethazine

R$_f$=0.33 (DCM:MeOH=10:1), RP-HPLC (betasil C18, 0.5 mL/min, 30-60% ACN in 10 min) 5.43 min, purity >99%, LC-MS (ESI, MH$^+$) 549.3. $^1$H NMR (500 MHz, CDCl$_3$) δ 1.04 (3H, d, J=6.5 Hz), 2.34 (3H, s), 2.66-2.72 (2H, m), 3.19-3.23 (1H, m), 3.38 (3H, s), 3.51-3.65 (22H, m), 3.70 (1H, dd, J=9.0, 13.0 Hz), 4.02 (1H, dd, J=4.0, 13.5 Hz), 6.91-6.94 (4H, m), 7.14-7.17 (4H, m).

mPEG$_7$-N-promethazine

R$_f$=0.33 (DCM:MeOH=10:1), RP-HPLC (betasil C18, 0.5 mL/min, 30-60% ACN in 10 min) 5.32 min, purity >99%, LC-MS (ESI, MH$^+$) 593.3. $^1$H NMR (500 MHz, CDCl$_3$) δ 1.04 (3H, d, J=6.5 Hz), 2.34 (3H, s), 2.64-2.73 (2H, m), 3.20-3.24 (1H, m), 3.38 (3H, s), 3.51-3.66 (26H, m), 3.70 (1H, dd, J=9.0, 13.0 Hz), 4.02 (1H, dd, J=4.0, 13.5 Hz), 6.91-6.94 (4H, m), 7.14-7.17 (4H, m).

mPEG$_9$-N-promethazine

R$_f$=0.33 (DCM:MeOH=10:1), RP-HPLC (betasil C18, 0.5 mL/min, 30-60% ACN in 10 min) 5.60 min, purity >99%, LC-MS (ESI, MH$^+$) 680.4. $^1$H NMR (500 MHz, CDCl$_3$) δ 1.04 (3H, d, J=6.5 Hz), 2.34 (3H, s), 2.64-2.73 (2H, m), 3.20-3.24 (1H, m), 3.38 (3H, s), 3.50-3.66 (34H, m), 3.69 (1H, dd, J=9.0, 13.5 Hz), 4.02 (1H, dd, J=4.0, 13.5 Hz), 6.91-6.94 (4H, m), 7.14-7.17 (4H, m).

Scheme 2: Synthesis of mPEG$_n$-N-Promethazine conjugates.

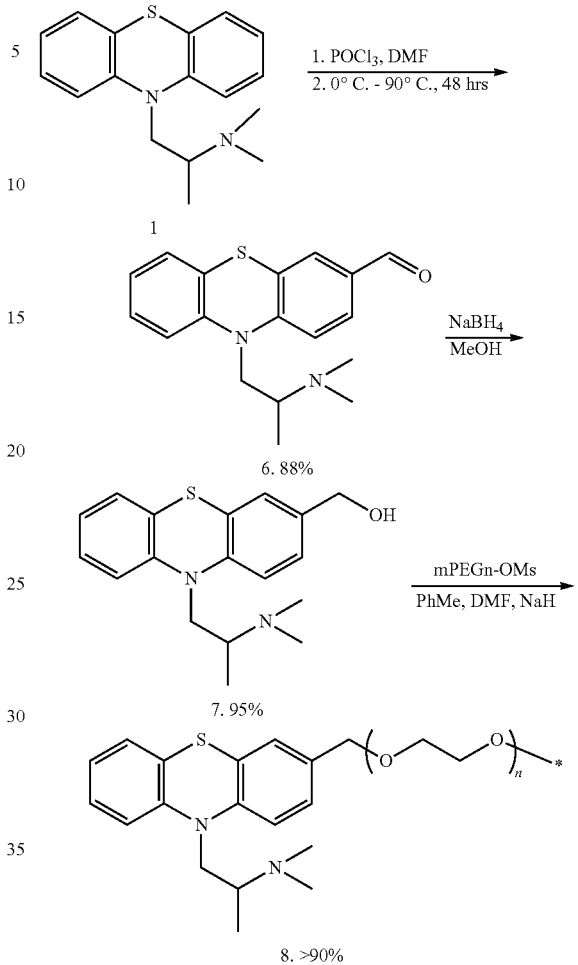

n = 3, 5, 7, 9

Vilsmeier Formylation:

Desalted promethazine (1.68 g, 5.92 mmol) was dissolved in DMF (1.92 mL, 24.9 mmol) in a 100-mL flask with a nitrogen bubble. The solution mixture was cooled down to 0° C. before a mixture of POCl$_3$ (1.41 mL, 15.4 mmol) and DMF (0.96 mL, 12.4 mmol) were added dropwise. The reaction solution was heated slowly to 90° C. for 6 hrs before an additional mixture of POCl$_3$ (1.5 mL) and DMF (0.8 mL) was added. The reaction was kept at this temperature and N$_2$ bubbled slowly during the next 40 hrs. The progress of the reaction was monitored by HPLC (SM<5% UV 254 nm, ELS ~100% conversion). The reaction was quenched by adding 30 g of ice and diluting with saturated NaHCO$_3$ (250 mL). NaOH (1N) was added until the pH reached 10-12. The resulting solution was then extracted by DCM (80 mL+50 mL×2). The combined organic phases were dried over Na$_2$SO$_4$. After filtration, the solution was concentrated and the DMF residue solution was loaded onto a Biotage 40S column and purified (2-7% MeOH in DCM in 16 CV). The product fractions were combined and concentrated to give a brownish product (1.63 g, 88% yield). HPLC analysis showed the starting material contamination is less than 3%.

(4-Aldehyde)-promethazine $R_f$=0.23 (DCM:MeOH=10:1), RP-HPLC (betasil C18, 0.5 mL/min, 10-60% ACN in 10 min) 7.75 min, LC-MS (ESI, MH$^+$) 313.2. $^1$H NMR (500 MHz, CDCl$_3$) δ 1.08 (3H, d, J=5.5 Hz), 2.35 (6H, s), 3.10 (1H, bs), 3.76 (1H, dd, J=4.0, 13.0 Hz), 4.14 (1H, bs), 6.96-7.02 (3H, m), 7.16-7.22 (2H, m), 7.64-7.69 (2H, m), 9.82 (1H, s).

Aldehyde Reduction:

The above aldehyde (1.63 g, 5.22 mmol) was dissolved in methanol (30 mL). NaBH$_4$ (433 mg, 12 mmol) was added at room temperature in small portions. The reaction was kept at room temperature for 15 min. The methanol solvent was evaporated and the residue was dissolved in NaHCO$_3$ (100 mL) and extracted with DCM (60 mL×3). The organic phase was combined and loaded onto a Biotage 40S column (2-20% MeOH in DCM in 20 CV). The two product peaks (same products) were combined and concentrated to give a colorless foam product (1.27 g, 77% yield).

(4-methylene hydroxyl)-promethazine $R_f$=0.19 (DCM:MeOH=10:1), RP-HPLC (betasil C18, 0.5 mL/min, 10-60% ACN in 10 min) 6.58+6.75 min, LC-MS (ESI, MH$^+$) 315.3. $^1$H NMR (500 MHz, CDCl$_3$) δ 1.07 (3H, d, J=6.5 Hz), 2.35 (6H, s), 3.09 (1H, bs), 3.68 (1H, dd, J=4.0, 13.5 Hz), 4.09 (1H, dd, J=3.5, 13.0 Hz), 4.59 (2H, s), 6.90-6.95 (3H, m), 7.15-7.18 (4H, m).

General Procedure for O-PEGylation from mPEG$_n$-OMs:

The above reductive product (about 200 mg, 1 eq) was combined with mPEG$_n$-OMs (1.2-1.5 eq) in 100-mL flask. The mixture was dissolved in toluene (30 mL) and azeotropic evaporated to about 2 mL. DMF (3 mL) and NaH (10 eq) was added. The reaction mixture was warmed up to 45° C. in an oil bath and the reaction was kept at this temperature for 6 hrs (or overnight). After removing the oil bath, the mixture was quenched with 30 g ice, diluted with saturated NaHCO$_3$ (60 mL), and extracted with DCM (20 mL×3). The combined DCM solution was dried over Na$_2$SO$_4$. After filtration, the solution was concentrated and the residue was purified on a Biotage 25M normal phase column (1-6% MeOH in DCM in 16 CV). The fractions (UV: >98% pure) were combined and loaded onto a Biotage reverse phase column (25M, 20% in 5 CV following with 20-65% acetonitrile in water in 20CV). The product fractions were combined and acetonitrile was evaporated until the solution become cloudy. The aqueous phase was then extracted with DCM (15 mL×3), each time a small amount of solid NaCl was added in extraction. The combined DCM solution was dried over Na$_2$SO$_4$ and filtered. The solution was then concentrated and dried under vacuum over 24 hrs before characterization.

mPEG$_3$-O-promethazine $R_f$=0.23 (DCM:MeOH=10:1), RP-HPLC (betasil C18, 0.5 mL/min, 10-60% ACN in 10 min) 8.27 min, purity >95%, LC-MS (ESI, MH$^+$) 461.3. $^1$H NMR (500 MHz, CDCl$_3$) δ 1.05 (3H, d, J=6.0 Hz), 2.34 (6H, s), 3.07 (1H, bs), 3.38 (3H, s), 3.54-3.56 (2H, m), 3.59-3.61 (2H, m), 3.64-3.70 (9H, m), 4.06 (1H, d, J=12.5 Hz), 4.52 (2H, s), 6.87-6.95 (3H, m), 7.12-7.16 (4H, m).

mPEG$_5$-O-promethazine $R_f$=0.23 (DCM:MeOH=10:1), RP-HPLC (betasil C18, 0.5 mL/min, 10-60% ACN in 10 min) 8.31 min, purity >97%, LC-MS (ESI, MH$^+$) 549.3. $^1$H NMR (500 MHz, CDCl$_3$) δ 1.07 (3H, d, J=5.5 Hz), 2.36 (6H, s), 3.10 (1H, bs), 3.37 (3H, s), 3.53-3.55 (2H, m), 3.59-3.61 (2H, m), 3.63-3.70 (17H, m), 4.09 (1H, d, J=9.0 Hz), 4.45 (2H, s), 6.88-6.95 (3H, m), 7.13-7.18 (4H, m).

mPEG$_7$-O-promethazine $R_f$=0.23 (DCM:MeOH=10:1), RP-HPLC (betasil C18, 0.5 mL/min, 10-60% ACN in 10 min) 8.39 min, purity >98%, LC-MS (ESI, MH$^+$) 637.4. $^1$H NMR (500 MHz, CDCl$_3$) δ 1.06 (3H, bs), 2.35 (6H, s), 3.08 (1H, bs), 3.38 (3H, s), 3.53-3.56 (2H, m), 3.59-3.61 (2H, m), 3.63-3.70 (25H, m), 4.06 (1H, bs), 4.45 (2H, s), 6.88-6.95 (3H, m), 7.13-7.18 (4H, m).

mPEG$_9$-O-promethazine $R_f$=0.23 (DCM:MeOH=10:1), RP-HPLC (betasil C18, 0.5 mL/min, 10-60% ACN in 10 min) 8.35 min, purity >99%, LC-MS (ESI, MH$^+$) 725.5. $^1$H NMR (500 MHz, CDCl$_3$) δ 1.05 (3H, d, J=3.5 Hz), 2.34 (6H, s), 3.07 (1H, bs), 3.38 (3H, s), 3.54-3.56 (2H, m), 3.59-3.61 (2H, m), 3.63-3.70 (33H, m), 4.06 (1H, dd, J=4, 13.0 Hz), 4.45 (2H, s), 6.87-6.94 (3H, m), 7.12-7.18 (4H, m).

Example 2

In Vitro Receptor Binding

Binding to Histamine Receptors

The receptor binding affinity of promethazine (parent) and N- and O-PEG derivatives are evaluated using radioligand binding assays in membranes prepared from CHO cells that express the recombinant human H1, H2, H3 or H4 histamine receptors. Competition binding experiments are conducted by incubating membranes with a fixed concentration of radioligand in the presence of variable concentrations of test compounds. The radioligands used are specific for each receptor subtype and the assay conditions are described in Table 2. Following incubations, the membranes are washed, and the bound radioactivity is measured. Non-specific binding is measured in the presence of excess cold ligand and subtraction of this value from the total binding yields the specific binding at each test compound concentration. IC$_{50}$ values are obtained from non-linear regression analysis of dose-response curves and are calculated only for those compounds that show >50% inhibition of binding at the highest concentrations. Ki is obtained using the Cheng Prusoff correction using experimental Kd vales that are determined under these assay conditions.

The binding affinities of Promethazine, mPEG-N-promethazine and mPEG-O-Promethazine conjugates to Histamine receptors is shown in Table 1. Promethazine and PEG-promethazine conjugates displayed high affinity binding to the H1 receptor. PEG conjugation results in a reduction in binding affinity and this effect is PEG size dependent.

Binding at the H2, H3 and H4 receptors is significantly lower for all molecules tested. Ki values could not be calculated at these receptors since <50% inhibition of binding is obtained at the highest concentrations tested.

TABLE 1

Binding affinities of Promethazine conjugates to Histamine receptors.

| Molecule | Ki (nM) | | | | Fold change in binding affinity at H1 |
|---|---|---|---|---|---|
| | H1 | H2 | H3 | H4 | |
| Promethazine | 0.278 | NS | NS | NS | 1 |
| mPEG$_3$-N-Promethazine | 2.28 | NS | NS | NS | 8.20 |
| mPEG$_4$-N-Promethazine | 1.95 | NS | NS | NS | 7.01 |
| mPEG$_5$-N Promethazine | 8.53 | NS | NS | NS | 30.68 |
| mPEG$_6$-N Promethazine | 13.2 | NS | NS | NS | 47.48 |
| mPEG$_7$-N Promethazine | 16.9 | NS | NS | NS | 60.79 |
| mPEG$_9$-N Promethazine | 44 | NS | NS | NS | 158.27 |
| mPEG$_3$-O-Promethazine | 7.62 | NS | NS | NS | 27.41 |
| mPEG$_5$-O-Promethazine | 7.16 | NS | NS | NS | 25.76 |
| mPEG$_7$-O-Promethazine | 33.2 | NS | NS | NS | 119.42 |
| mPEG$_9$-O-Promethazine | 45.1 | NS | NS | NS | 162.23 |

NS: No significant binding

TABLE 2

Assay Conditions for histamine receptor binding assays

| Receptor | Receptor Source | Radioligand | Non-specific binding | Methods | Test Conc. |
|---|---|---|---|---|---|
| Histamine H1 | Human rCHO cells | [$^3$H]-Pyrilamine (1.2 nM) | Pyrilamine (1 μM) | Reaction in 50 mM Tris-HCl (pH 7.4), 2 mM $MgCl_2$, 100 mM NaCl and 250 mM Sucrose at 25° C. for 3 h. | 0.01, 0.1, 0.3, 1, 3, 10, 30, 100 nM, 3, 30 μM |
| Histamine H2 | Human rCHO-K1 cells | [$^{125}$I]-Aminopotentidine (0.1 nM) | Tiotidine (3 μM) | Reaction in 50 mM phosphate (pH 7.4) at 25° C. for 2 h. | 0.01, 0.1, 0.3, 1, 3, 10, 30, 100 nM, 3, 30 μM |
| Histamine H3 | Human rCHO-K1 cells | [$^3$H]R(−)-α-Methylhistamine (3 nM) | R(−)-α-Methylhistamine (1 μM) | Reaction in 50 mM Tris-HCl (pH 7.4), 5 mM $MgCl_2$, 0.04% BSA at 25° C. for 1.5 h. | 0.01, 0.1, 0.3, 1, 3, 10, 30, 100 nM, 3, 30 μM |
| Histamine H4 | Human rCHO-K1 cells | [$^3$H]Histamine (8.2 nM) | Histamine (1 μM) | Reaction in 50 mM Tris-HCl (pH 7.4), 1.25 mM EDTA at 25° C. for 1.5 h. | 0.01, 0.1, 0.3, 1, 3, 10, 30, 100 nM, 3, 30 μM | rCHO—recombinant CHO cells

Binding to Muscarinic Receptors

The receptor binding affinities of Promethazine (parent) and PEG-Promethazine conjugates are evaluated using radioligand binding assays in membranes prepared from CHO cells that express the recombinant human M1, M2, M3, M4 or M5 muscarinic acetylcholine receptors. Competition binding experiments are conducted by incubating membranes with a fixed concentration of radioligand in the presence of variable concentrations of test compounds. $^3$H—N-Methylscopolamine at 0.8 nM is used as the radioligand for all receptor subtypes. Incubations are carried out for 2 hours at 25° C. in buffer containing 50 mM Tris HCl, 10 mM $MgCl_2$ and 1 mM EDTA. Following incubations, the membranes are washed, and the bound radioactivity is measured. Non-specific binding is measured in the presence of excess Atropine as the cold ligand and subtraction of this value from the total binding yields the specific binding at each test compound concentration. $IC_{50}$ values are obtained from non-linear regression analysis of dose-response curves and are calculated only for those compounds that show >50% inhibition of binding at the highest concentration tested. Ki is obtained using the Cheng Prusoff correction using Kd values that are experimentally determined under these assay conditions.

The binding affinities of Promethazine, mPEG-N-promethazine and mPEG-O-Promethazine conjugates at the five muscarinic receptor subtypes are shown in Table 3. Promethazine displays high binding affinity to all muscarinic receptor subtypes, with Ki values ranging from ~7-26 nM and displays little selectivity for any muscarinic receptor subtype. In contrast, the PEG conjugates display a reduction in binding affinity at all subtypes—the Ki at any particular receptor subtype was reduced about 10-100-fold. In several cases, an inhibition of radioligand binding could not be obtained at the highest concentration tested and hence data are shown as "no significant binding (NS)". These data suggest that PEG conjugation reduces the binding affinity of promethazine conjugates to muscarinic acetylcholine receptors.

TABLE 3

Binding affinities of Promethazine conjugates to muscarinic receptors.

| | Ki (nM) | | | | |
|---|---|---|---|---|---|
| Molecule | M1 | M2 | M3 | M4 | M5 |
| Promethazine | 8.18 | 26.4 | 16.2 | 7.74 | 9.34 |
| mPEG$_3$-N-Promethazine | NS | NS | NS | NS | NS |
| mPEG$_4$-N-Promethazine | NS | NS | NS | NS | NS |
| mPEG$_5$-N-Promethazine | NS | 817 | NS | NS | NS |
| mPEG$_6$-N-Promethazine | NS | 337 | NS | NS | 1740 |
| mPEG$_7$-N-Promethazine | NS | 90 | NS | 435 | 905 |
| mPEG$_9$-N-Promethazine | NS | 308 | NS | 455 | 2050 |
| mPEG$_3$-O-Promethazine | NS | NS | NS | NS | NS |
| mPEG$_5$-O-Promethazine | NS | NS | NS | NS | NS |
| mPEG$_7$-O-Promethazine | NS | NS | NS | NS | NS |
| mPEG$_9$-O-Promethazine | NS | NS | NS | NS | NS |

NS: No significant binding

Example 3

Scale up of mPEG$_4$-N-promethazine

Materials: Promethazine hydrochloride, 1-chloroethyl chloroformate were purchased from Sigma-Aldrich (St Louis, Mo.). mPEG$_4$-Br was received from India Sai CRO. Sodium bicarbonate (NaHCO$_3$), sodium sulfate (Na$_2$SO$_4$), sodium chloride (NaCl), Potassium carbonate (K$_2$CO$_3$), Sodium hydroxide (NaOH), and hydrochloride acid (HCl) were purchased from EM Science (Gibbstown, N.J.). Toluene, dichloroethylene (DCE), dichloromethane (DCM), and other organic solvents were used as they purchased.

Desalting Promethazine

The reaction was carried out in NaHCO$_3$/DCM. The product was solidified in high vacuo drying.

Demethylation and Product Precipitation:

The desalted promethazine (13.16 g, 46.3 mmol) was added to a 1000-mL flask. Toluene (110 mL) and DCE (100 mL) were added and azeotropically distilled while under 45° C. then followed with distillation under high vacuum for an additional 15 min. DCE (100 mL) was added and after a homogenous solution was obtained, 1-chloroethyl chloroformate (25 g×6, 1.06 mol) was added. The reaction mixture was heated to 105° C. and allowed to reflux for 18 hours. The reaction was allowed to cool to approximately 50° C. at which point the solvent was removed by rotary evaporation and then subsequently under high vacuum for 3 hrs before additional DCE (100 mL) and ethanol (100 mL) were added. The solution was kept under 83° C. and refluxed for another 18 hrs. The solvent was removed while keeping the temperature under 55° C. and the resulting residue was dissolved in 0.2N HCl. The aqueous phase was washed with ether (200 mL×5). A salt-like precipitate was generated while extracting the aqueous phase with DCM. The precipitate was collected by filtration and washed with DCM. The DCM solution was evaporated and heated to 50° C. The precipitation process was repeated. The salt-like product was basified in NaHCO$_3$ (3 piece of NaOH) and extracted with DCM (100 mL×3). The combined DCM was dried over Na$_2$SO$_4$. Filtration, evaporation, and drying under high vacuum give an oily-like product (~10.0 grams, 79% yield).

N-Demethyl-promethazine:

RP-HPLC (betasil C18, 0.5 mL/min, 30-60% ACN in 10 min) 4.31 min, LC-MS (ESI, MH$^+$) 271.1. $^1$H NMR (500 MHz, CDCl$_3$) δ 1.14 (3H, d, J=6.5 Hz), 2.37 (3H, s), 3.03-3.09 (1H, m), 3.81 (1H, dd, J=5.0, 13.5 Hz), 3.88 (1H, dd, J=8.0, 13.5 Hz), 6.92-6.96 (4H, m), 7.15-7.19 (4H, m).

N-Alkylation and Purification.

The demethylation product (2.06 g, 7.62 mmol) was mixed with mPEG$_4$-Br (2.53, 9.33 mmol). Water (10 mL) was premixed with K$_2$CO$_3$ (5.37 g, 38.9 mmol) and the resulting solution was added to the above mixture. The water solution was heated in oil bath while the temperature remained under 100° C. The reaction was kept at this temperature for 20 hrs and HPLC analysis indicated the reaction was complete. The product residue was dissolved in DCM and the aqueous phase separated. The DCM was removed under reduced pressure and the resulting residue was dissolved in 0.3N HCl (240 mL) and washed with ether (100 mL×3). Then the aqueous solution was washed with a mixture of EtOAc and ether (2 times). The aqueous phase was basified with solid NaOH to pH >10 and extracted with DCM (50 mL×3). The combined DCM phase was washed with a saturated solution of NaHCO$_3$ (50 mL×5+1 piece of NaOH-100 mg each time). The DCM phase was separated, dried over Na$_2$SO$_4$, and the solvent removed under reduced pressure. A slight yellowish product (2.9 g) was obtained after the high vacuo drying with >99% purity.

mPEG$_4$-N-promethazine

RP-HPLC (betasil C18, 0.5 mL/min, 30-60% ACN in 10 min) 6.23 min, purity >99%, LC-MS (ESI, MH$^+$) 461.1. $^1$H NMR (500 MHz, CDCl$_3$) δ 1.04 (3H, d, J=6.5 Hz), 2.34 (3H, s), 2.67-2.71 (2H, m), 3.20-3.23 (1H, m), 3.38 (3H, s), 3.50-3.67 (14H, m), 3.70 (1H, dd, J=9.0, 13.5 Hz), 4.03 (1H, dd, J=4.5, 13.0 Hz), 6.91-6.94 (4H, m), 7.14-7.18 (4H, m).

Example 4

Scale Up Synthesis of mPEG$_3$-promethazine

Materials: Promethazine hydrochloride, 1-chloroethyl chloroformate were purchased from Sigma-Aldrich (St Louis, Mo.). mPEG$_3$-Br was received from CRO-Sai Advandium in india. The other inorganic salts, base, acid and organic solvents were used as purchased.

Desalting of Promethazine HCl

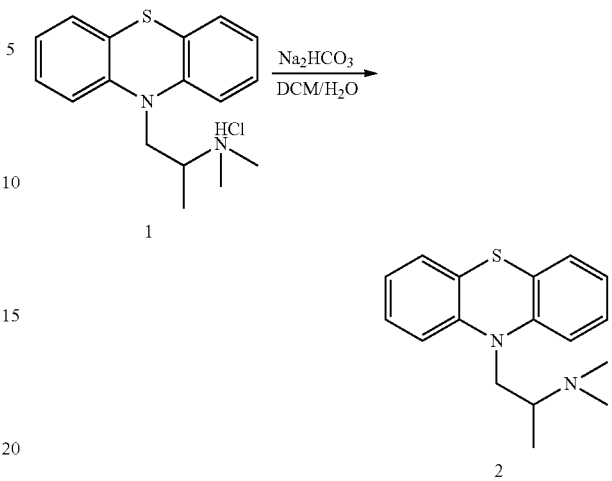

Promethazine HCl (20.2723 g, 63.2 mmol) was dissolved in DCM (250 mL), washed with aq. 10% Na$_2$HCO$_3$ solution (2×150 mL). The aq. solution was extracted with DCM (50 mL). The combined organic solution was dried over Na$_2$SO$_4$, concentrated to dryness. The residue was mixed with toluene (150 mL), concentrated to dryness and dried under high vacuum to afford 18.6892 g of promethazine in 96% yield.

Demethylation of Promethazine

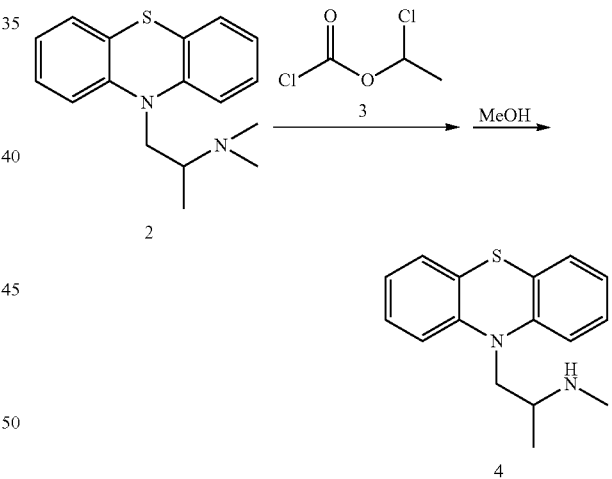

First Run:

Promethazine (10.743 g, 36.3 mmol) was dissolved in dichloroethane (150 mL) at room temperature, cooled to 0° C. 1-Chloroethyl chloroformate (100 g, 4 bottles of 25 g per bottle, 685 mmol) was added slowly. The reaction mixture became green in color after a few minutes and then became more yellow. The mixture was stirred at room temperature for 2 h, refluxed for 19 h (oil bath temp. 100 OC). HPLC analysis showed low conversion and some side products. The reaction mixture was concentrated to remove some DCE (~120 mL). More of 1-chloroethyl chloroformate (25 g, 171 mmol) was added. The mixture was stirred at 115° C. for 22 h. HPLC analysis didn't show starting material. The mixture was concentrated to remove all of solvents under reduced pressure and dried under high vacuum.

The crude mixture was dissolved in MeOH (100 mL) at room temperature and stirred at room temperature for 15 min (open flask) then refluxed for 18 h (oil bath temperature: 75 degree), cooled to room temperature. The mixture was concentrated to remove all of solvents, the residue was dissolved in DCM (250 mL), washed with 10% aq. $NaHCO_3$ solution (2×100 mL), concentrated to dryness. The residue was dissolved in 750 mL of 0.2 N HCl solution, washed with ether (3×150 mL). The aqueous solution was extracted with DCM, and adjusted the mixture to basic with aq. KOH solution, extracted again with DCM (3 times) until no product was found in DCM solution by TLC. All of organic solutions were combined and dried over $Na_2SO_4$, concentrated to afford 8.5066 g of the product as oil. The yield was 92%.

Second Run:

Promethazine (7.9456 g, 26.8 mmol) was mixed with 1-chloroethyl chloroformate (20 g, 137 mmol). The mixture was stirred at 120° C. (oil temperature) for 17.5 h. HPLC showed the reaction was complete. The reaction was cooled and concentrated. The residue was dried under high vacuum.

The resulting residue was dissolved in MeOH (100 mL), refluxed for 2 h, cooled to r.t. The mixture was concentrated to remove all of solvent to afford a solid. The solid was mixed with 0.2 N HCl solution. Some of solid didn't dissolve in the acidic solution. The mixture was filtered and the solid was washed with ether and then dissolved in DCM. The aq. solution was washed with ether (2×150 mL). The aq. solution was adjusted pH to 10-11 with aq. KOH solution, and then extracted with DCM (4×150 mL). The combined DCM solution was dried over $Na_2SO_4$, concentrated to yield an oil. The oil product was dissolved in 0.2 N HCl (500 mL). The solution was washed with ether (2×150 mL), and adjusted the pH to 11.32 with aq. KOH solution, extracted with DCM (4×150 mL), dried over $Na_2SO_4$, concentrated to afford 4.9763 g of product in 69% yield.

$^1$H-NMR ($CDCl_3$, 500 MHz): 7.181-7.138 (m, 4H, Ar—H), 6.951-6.915 (m, 4H, Ar—H), 3.886-3.785 (m, 2H, $CH_2$), 3.067-3.028 (m, 1H, CH), 2.358 (s, 3H, $CH_3$), 1.127 (d, J=6.0 Hz, $CH_3$).

Synthesis of mPEG$_3$-N-promethazine

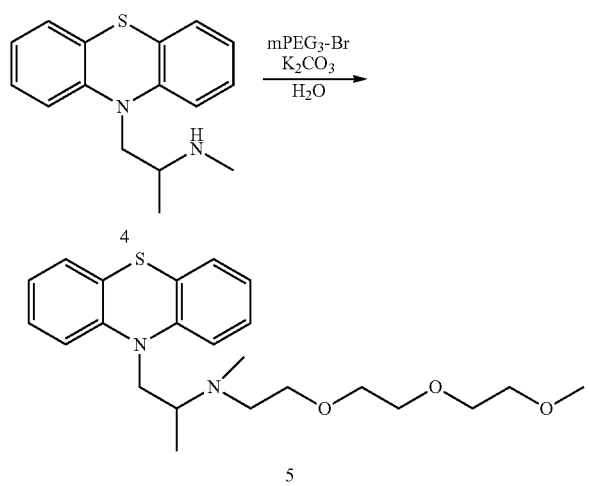

First Run:

Demethylpromethazine (1.7301 g, 6.4 mmol) and mPEG$_3$-Br (1.7877 g, 7.87 mmol) were placed in a 25-mL vial. A solution of $K_2CO_3$ (5.47 g, 39.6 mmol) in water (10 mL) was added. The resulting mixture was stirred at room temperature for 68.5 h. HPLC showed only about 30% starting material remained. The mixture was heated at 120° C. for 50 min under microwave conditions. HLPC showed the reaction was complete. When the reaction mixture was cooled to room temperature, EtOAc (50 mL) was added. The mixture was washed with 0.2 N HCl (100 ml). The aq. solution only contained impurities based on HPLC; therefore, the organic EtOAc solution was extracted with 0.2N HCl solution (2×150 mL). The combined aq. extraction solution was washed once again with EtOAc (100 mL) and adjusted the pH to 11.84 with aq. KOH solution, extracted with DCM (3×60 mL). The combined DCM solution was dried over $Na_2SO_4$, and concentrated to afford 2.3094 g of product in 87% yield.

Second Run:

Demethylpromethazine (6.4773 g, 23.96 mmol) and mPEG$_3$-Br (5.983 g, 16.30 mmol) were placed in a 100-mL round bottomed flask. A solution of $K_2CO_3$ (17.34 g, 125 mmol) in water (35 mL) was added. The resulting mixture was stirred at 110° C. (oil temperature) for a few hours. The mixture was stirred at 100° C. for 1.5 h at which point more mPEG$_3$-Br (0.643 g, 2.83 mmol) was added. The mixture was stirred at 105° C. for 2.5 h. The reaction mixture was cooled and EtOAc (150 mL) was added. The aq. solution was separated and the organic solution was washed once with 5% aq. $NaHCO_3$. The EtOAc solution was extracted with 0.2 N HCl (3×150 mL). The combined acidic solution was washed with EtOAc (2×100 mL), and then adjusted pH to 10-11 with aq. KOH solution, extracted with DCM (4×200 mL). The combined DCM solution was dried over $Na_2SO_4$, concentrated to afford 9.2668 g of final product as oil in 93% yield.

$^1$H-NMR ($CDCl_3$, 500 MHz): 7.170-7.139 (m, 4H, Ar—H), 6.935-6.902 (m, 4H, Ar—H), 4.021 (dd, J=4.5 and 13.5 Hz, 1H), 3.690 (dd, J=9.0 and 13.5 Hz, 1H), 3.648-3.576 (m, 6H), 3.560-3.486 (m, 4H), 3.273 (s, 3H, $CH_3$), 3.246-3.181 (m, 1H), 2.732-2.643 (m, 2H, $CH_2$), 2.332 (s, 3H, $CH_3$), 1.034 (d, J=6.5 Hz, 3H, $CH_3$). LC-MS: 417.3 ($MH^+$).

Example 5

Analgesic Assay

An analgesic assay was used to determine whether a given compound can reduce and/or prevent visceral pain in mice.

The assay utilized CD-1 male mice (5-8 mice per group), each mouse being approximately 0.015-0.030 kg on the study day. Mice were treated according to standard protocols.

Mice were given a single "pretreatment" dose of a compound lacking covalent attachment of a water-soluble, non-peptidic oligomer, a corresponding version comprising the compound covalently attached to a water-soluble, non-peptidic oligomer, or control solution (IV, SC, IP or orally) thirty minutes prior to the administration of the acetic acid solution. The animal was given an IP injection of an irritant (acetic acid) that induces "writhing" which may include: contractions of the abdomen, twisting and turning of the trunk, arching of the back and the extension of the hindlimbs. Mice were given a single IP injection (0.1 mL/10 g bodyweight) of a 0.5% acetic acid solution. After the injection the animals were returned to their observation enclosure and their behavior was observed. Contractions were counted between 0 and 20 minutes after the injection.

The animals were used once. Each tested article was dosed at different doses, when possible. The results are shown in the table below.

TABLE

Acetic Acid Writhing Data

| TA | Promethazine Parent | | PEG$_3$-N-Pro | PEG$_4$-N-Pro | PEG$_5$-N-Pro | PEG$_6$-N-Pro | PEG$_7$-N-Pro | PEG$_9$-N-Pro | PEG$_3$-O-Pro | PEG$_5$-O-Pro | PEG$_7$-O-Pro | PEG$_9$-O-Pro |
|---|---|---|---|---|---|---|---|---|---|---|---|---|
| Dose (mg/kg) | 1 | 3 | 5 | 10 | 10 | 10 | 10 | 10 | 10 | 10 | 10 | 10 | 10 |
| Mean (% Morphine) | 0.5814 | 147.1 | 119.0 | 119.0 | 100.6 | 49.14 | 88.00 | 68.00 | 64.57 | −59.69 | 13.12 | 90.82 | 28.42 | 44.32 |
| SD | 132.5 | 63.69 | 0.0 | 0.0 | 41.42 | 57.26 | 50.04 | 34.79 | 78.00 | 62.30 | 50.11 | 43.45 | 81.70 | 62.87 |
| SEM | 59.27 | 28.48 | 0.0 | 0.0 | 18.53 | 25.61 | 22.38 | 15.56 | 34.88 | 27.86 | 22.41 | 19.43 | 36.54 | 28.11 |

Example 6

Brain:Plasma Ratio for PEG-Promethazine Conjugates

The ability of the PEG-promethazine conjugates to cross the blood brain barrier (BBB) and enter the CNS was determined by measuring the ratio of their relative concentrations in brain and plasma in rats. Briefly, rats were injected intravenously with 5 mg/kg of promethazine, PEG-promethazine conjugates or atenolol. An hour following injection, the animals were sacrificed and plasma and brain were collected and frozen immediately. Following tissue and plasma extractions, concentrations of the compounds in brain and plasma were measured using LC-MS/MS. The brain:plasma ratio was calculated as the ratio of measured concentrations in the brain(ng/g) and plasma (ng/mL). Atenolol, which does not cross the blood brain barrier is used as a measure of vascular contamination of the brain tissue.

The following table shows the ratios of brain to plasma concentrations of PEG-Promethazine conjugates. The brain:plasma ratio of promethazine is 39.93:1, indicating a nearly 40 fold greater concentration of promethazine in the brain compared to the plasma compartment. PEG conjugation reduced the entry of promethazine into the CNS as evidenced by 20-500-fold lower brain:plasma ratios of the PEG-promethazine conjugates.

| | Brain/plasma ratio | | |
|---|---|---|---|
| Compound | Mean | Std. Dev. | N |
| Promethazine | 39.926 | 13.286 | 3 |
| mPEG$_4$-N-Promethazine | 1.863 | 0.470 | 3 |
| mPEG$_5$-N-Promethazine | 0.243 | 0.058 | 3 |
| mPEG$_6$-N-Promethazine | 0.098 | 0.027 | 3 |
| mPEG$_7$-N-Promethazine | 0.112 | 0.009 | 3 |
| mPEG$_9$-N-Promethazine | 0.080 | 0.023 | 3 |
| Atanolol | 0.024 | 0.006 | 3 |

Example 7

In Vivo Efficacy of PEG-Promethazine Conjugates

The antihistamine efficacy of PEG-Promethazine conjugates is evaluated in vivo by their ability to antagonize bronchoconstriction induced by histamine in guinea pigs. Groups of 3-4 guinea pigs are anesthetized with urethane, demobilized by succinylcholine, and placed on a heated plate to keep body temperature at 37° C. The left carotid artery is cannulated with a catheter (PE50, inner diameter 0.58 mm) connected to a pressure transducer for measurements of blood pressure (BP). A cannula (20 mm in length and with a 2 mm inner diameter) is inserted into the upper trachea through a tracheotomy and connected to a constant-volume mechanical ventilator. A respiratory volume of 10 ml/kg and a frequency of 50 breaths per minute are used with animals placed in a supine position. Respiratory air flow is measured using a flow transducer connected to a pneumotachograph. Pleural pressure is measured using a differential pressure transducer connected to two catheters, one through a 3-way stopcock connecting the pneumotachograph and trachea for obtaining intrapulmonary pressure, another from a catheter which is directly inserted into the pleural cavity for obtaining intrapulmonary pressure. Tidal volume (VT) is calculated by integration of the flow signal. Lung resistance ($R_L$) is calculated from pleural pressure ($\Delta P$) and flow signals ($\Delta F$) measured at isovolumetric points (50%) during inspiration and expiration, i.e., $R_L = \Delta P/\Delta F$. Dynamic Compliance ($C_{dyn}$) is the amount of lung expansion (volume change) per unit of pleural pressure change when the pressure and volume changes are measured at times of zero flow. Briefly, dividing tidal volume (VT) with transpulmonary pressure ($\Delta PTP$) between points of zero flow yields $C_{dyn} = VT/\Delta PTP$. All signals are captured by a data acquisition and analysis system (PO-NE-MAH Inc., USA).

PEG-Promethazine conjugates are administered intra-tracheally, subcutaneously or orally at various times prior to an IV histamine challenge. The various parameters ($R_L$, $C_{dyn}$, BP, HR) are recorded immediately before administration of test substance and vehicle as well as immediately before (0 min) and at 0.33, 0.67, 1, 2, 3, 4 and 5 minutes following challenge with histamine phosphate (10 µg/kg, 1 ml/kg, intravenously). Histamine produces a pronounced bronchoconstriction in guinea pigs measured as a decrease in pulmonary compliance and increase in pulmonary resistance that is dose-dependently antagonized by molecules with antihistamine activity.

Example 8 pKa and Log P Determination for Promethazine and PEG Promethazine Conjugates

The Sirius GLpKa instrument is used to determine the pKa and Log P for Promethazine and Peg Promethazine conjugates. A blank standardization has to be completed first and passed in order to conduct the compound experiments. The solutions used by the instrument for the blank titration include water, a pH solution, and a surfactant (TRITON X-100). The TRITON X-100 was purchased commercially from Sirus. The 0.5% solution of TRITON X-100 was used in the experiment. In a 1 L volumetric flask 5 mls of TRITON X-100 is added and MILLI Q water to volume. The vessels used by the instrument were filled to ⅓ of their volume with each solution. Therefore the assay tray contains one vessel for water, pH solution, and surfactant for the blank run. The temperature of the water bath for the instrument is 25° C. The blank is calculated as an average of three "good" experiments. The "good" was denoted by a green check mark next to the assay number in the computer software. Once the blank was run successfully the instrument was ready to conduct the experiments.

The pKa had to be determined first in order to calculate the Log P. The ΔPI is used to determine the pKa needed for the Log P experiment followed by the conjugates. Promethazine was first weighed into a vessel. The amount weighed for each sample was 10% of the molecular weight of the compound (i.e. 2.84 g for Promethazine). The same procedure was followed for each PEG-Promethazine conjugate n=3-9. The vessels were placed in the assay tray of the instrument. A method had to be set up for the pKa run. The experimental parameters are entered into the computer software. These included sample weight, molecular weight, assay type (aqueous pKa), number of assays (three), and titration range (generally 3.5-12). The run was started. There are three measurements for each run that are averaged to obtain the final results from the data points collected in the calculation software. All runs were denoted as "good" by the green check mark next to the assay number. The pKa values were obtained for all compounds as listed in the table below.

An additional method has to be set up for the Log P determinations for each compound. The Promethazine and PEG-Promethazine conjugates (n=3-9) are weighed into vessels in the same manner as for the previous experiment, i.e., 10% of the molecular weight. The vessels are placed in the assay tray of the instrument. The experimental parameters are entered into the computer. These included sample weight, molecular weight, assay type (Partition Log P), number of assays (three), and pKa value of the parent drug from the previous experiment. The run was started. There are three measurements for each run that are averaged to obtain the final results from the data points collected in the calculation software. All runs were denoted as "good" by the green check mark next to the assay number. The Log P values were obtained for all compounds as listed in the table below.

| Compound Description | MW | pKa | LogP |
|---|---|---|---|
| Promethazine | 284.4 | 8.988 | 3.431 |
| mPEG$_3$-N-Promethazine | 416.58 | 8.405 | 3.654 |
| mPEG$_4$-N-Promethazine | 460.6 | 8.448 | 3.511 |
| mPEG$_5$-N-Promethazine | 504 | 8.674 | 3.598 |
| mPEG$_6$-N-Promethazine | 548.7 | 8.529 | 3.250 |
| mPEG$_7$-N-Promethazine | 592.8 | 8.486 | 2.995 |
| mPEG$_8$-N-Promethazine | 636 | 8.238 | 2.648 |
| mPEG$_9$-N-Promethazine | 680.9 | 8.296 | 2.540 |

What is claimed is:

1. A method of treating allergic reactions, anaphylaxis, motion sickness, nausea, or visceral pain comprising administering to a subject in need thereof a therapeutically effective amount of a compound having the formula:

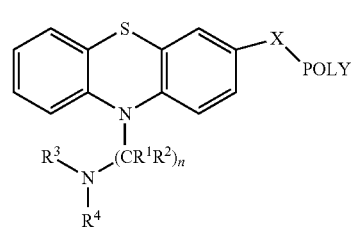

Formula Ib-C $R^1$, $R^2$, $R^3$, and $R^4$, each independently are selected from the group consisting of hydrogen, unsubstituted alkyl, and substituted alkyl; or $R^3$ and $R^4$ together with the nitrogen form a heterocycle;

n is an integer equal to or greater than one;

X is a spacer moiety; and

POLY is a poly(ethylene oxide) polymer.

2. The method of claim 1, wherein said administering is selected from parenteral, oral, transdermal, and rectal.

3. The method of claim 2, wherein said parenteral administering is selected from intravenous and intramuscular injection.

4. The method of claim 1, wherein said administering is orally administering.

5. The method of claim 1, wherein administering comprises administering about 0.001 mg/day to 1000 mg/day.

6. The method of claim 1, wherein administering comprises administering about 0.10 mg/day to 500 mg/day.

7. The method of claim 1, wherein administering comprises administering on a dosing schedule selected from five times a day, four times a day, three times a day, twice daily, once daily, three times weekly, and twice weekly.

8. The method of claim 1, wherein the poly(ethylene oxide) is a poly(ethylene glycol) polymer.

9. The method of claim 1, wherein the poly(ethylene oxide) is made of from about 1 to about 30 monomers.

10. The method of claim 9, wherein the poly(ethylene oxide) is made of from about 1 to about 10 monomers.

11. The method of claim 1, wherein an alkoxy or hydroxy end-capping moiety is attached to the poly(ethylene oxide) polymer.

12. The method of claim 1, wherein a single poly(ethylene oxide) polymer is attached to the phenothiazine residue.

13. The method of claim 1, wherein more than one poly(ethylene oxide) polymer is attached to the phenothiazine residue.

14. The method of claim 1, wherein the linkage is selected from an ether linkage and an ester linkage.

15. The method of claim 1, wherein POLY is —(CH$_2$CH$_2$O)$_n$Y, wherein Y is selected from H and —CH$_3$; and n is 1 to 30.

16. The method of claim 1, wherein X is —O— or a bond.

17. The method of claim 1, having the formula:

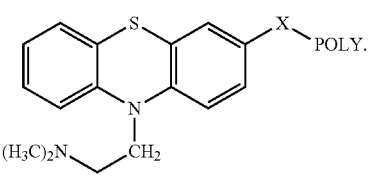

18. The method of claim 1, having the formula:
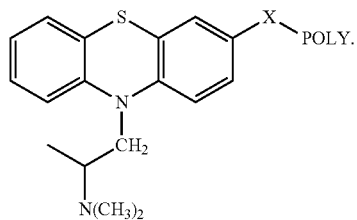
* * * * *